(12) United States Patent
Abdel-Magid et al.

(10) Patent No.: US 6,384,233 B1
(45) Date of Patent: May 7, 2002

(54) PROCESS FOR PREPARING 1,5-DIARYL-3-SUBSTITUTED PYRAZOLES

(76) Inventors: Ahmed F. Abdel-Magid, 1383 Jasper Dr., Ambler, PA (US) 19002; Bruce D. Harris, 80 W. Baltimore Ave., Apt. B612, Lansdowne, PA (US) 19050; Cynthia A. Maryanoff, 4029 Devonshire Dr., Buckingham Township, PA (US) 18922

( * ) Notice: Subject to any disclaimer, the term of this patent is extended or adjusted under 35 U.S.C. 154(b) by 0 days.

(21) Appl. No.: 09/966,116

(22) Filed: Sep. 28, 2001

Related U.S. Application Data

(63) Continuation of application No. 09/629,997, filed on Aug. 1, 2000, now abandoned
(60) Provisional application No. 60/146,997, filed on Aug. 3, 1999.

(51) Int. Cl.$^7$ ............................................. C07D 231/12
(52) U.S. Cl. .................................................... 548/375.1
(58) Field of Search ....................................... 548/375.1

(56) References Cited

U.S. PATENT DOCUMENTS

| | | |
|---|---|---|
| 4,826,868 A | 5/1989 | Wachter et al. |
| 4,898,952 A | 2/1990 | Murray et al. |
| 5,117,054 A | 5/1992 | Murray |
| 5,843,958 A | 12/1998 | Ferro et al. |

OTHER PUBLICATIONS

Yale, Harry L., The Hydroxamic Acids, Chem. Rev., 1943, 33, 209–257.
Nikishin, G.I, Troyansky, E.I, Svitanko, I.V. & Chizhov, O.S., N,O–Acylotropy in N–Methylpentanehydroxamic Acid, Tetrahedron Lett., 1984, 25, 97–98.
Murray, W.V. & Wachter, M.P., A Simple Regioselective Synthesis of Ethyl 1,5–Diarylpyrazole–3–carboxylates, Heterocyclic Chem., 1989, 26, 1389–1392.
Robinson, Tepoxalin, Drugs of the Future, 1990, 15, 9, 902–903.
Murray, W.V., Hadden, S.K., Wachter, M.P., Synthesis of 3–(1,5–Diphenyl–3–pyrazolyl)aryl Propanoates, J. Heterocyclic Chem., 1990, 27, 1933–1940.
Murray, W.V., Wachter, M.P., Synthesis and Properties of Aryl–1,3–dioxo Carboxylic Acids, J. of Org. Chem., 1990, 55, 3424–3426.
Murray, W., Wachter, M., Barton, D., Forero–Kelly, Y., The Regioselective Synthesis of Tepoxalin, 3–[5–(4–Chlorophenyl)–1–(4–methoxyphenyl)–3–pyrazolyl]–N–hydroxy-N-methylpropanamide and Related 1,5–Diarylpyrazole Anti–inflammatory Agents, Synthesis, 1991, 18–20.
Murray, W.V. & Hadden, S.K., A Facile Synthesis of Tepoxalin, 5–(4–Chlorophenyl)–N–hydroxy–1–(4–methoxyphenyl)–N–Methyl–1H–pyrazole–3–propanamide, J. of Org. Chem. 1992, 57, 6662–6663.
Murray, W.V., The Synthesis of 3–[3–(4–Chlorophenyl)–1–(4–methoxyphenyl)–5–pyrazolyl]–N–hydroxy a Regioisomer of Tepoxalin, Tetrahedron Lett., 1993, 34, 1863–1866.
Burinsky, D.J., Armstrong, B.L., Oyler, A.R., & Dunphy, R., Characterization of Tepoxalin and its Related Compounds by High Performance Liquid Chromatography/Mass Spectrometry, Journal of Pharmaceutical Sciences, vol. 85, No. 2, Feb. 1996, p. 159–164.

*Primary Examiner*—Robert W. Ramsuer
(74) *Attorney, Agent, or Firm*—Ellen Ciambrone Coletti

(57) ABSTRACT

A process for making a compound of formula I wherein the substituents are as described in the specification comprising reacting a ketone of formula II with succinic anhydride and an alkoxide base to form a compound of formula III

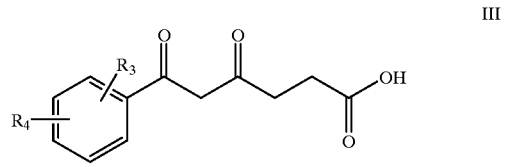

which is reacted with a compound of formula IV to form a compound of V

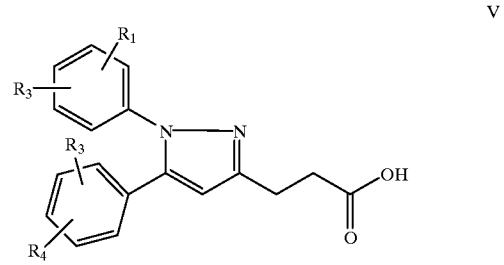

and reacting with an alcohol to form the corresponding ester of formula VI

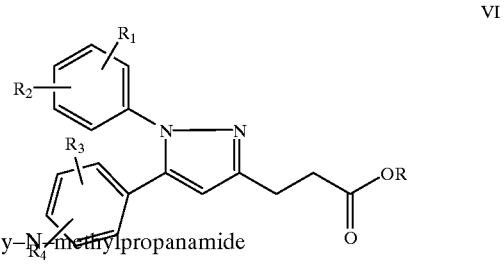

and reacting the ester with N-methylhydroxylamine.

4 Claims, No Drawings

PROCESS FOR PREPARING 1,5-DIARYL-3-SUBSTITUTED PYRAZOLES

CROSS REFERENCE TO RELATED APPLICATIONS

This application is the continuation application of U.S. application Ser. No. 09/629,997, filed Aug. 1, 2000, now abandoned, which application claims the benefit U.S. Provisional application Ser. No. 60/146,997, filed on Aug. 3, 1999.

BACKGROUND OF THE INVENTION

FIELD OF THE INVENTION

The invention relates to a process of preparing 1,5-diaryl-3-substituted pyrazoles of the formula

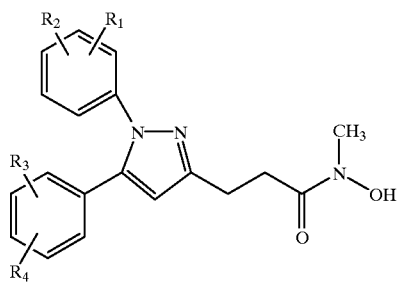

I wherein
$R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, omega-trifluoromethyl lower alkoxy, or where $R_1$, $R_2$ or $R_3$, $R_4$ taken together with the phenyl group to which they are attached, form a naphthyl or substituted naphthyl group.

In a preferred embodiment, the invention relates to a process of making 5-(4-chlorophenyl)-N-hydroxy-1-(4-methoxyphenyl)-N-methyl-1H-pyrazole-3-propanamide, a compound of formula Ia, known as tepoxalin.

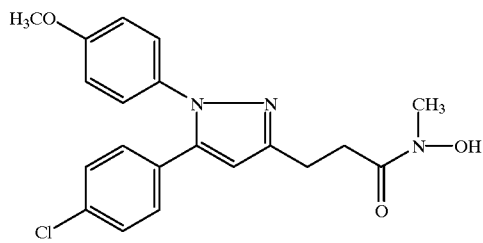

Ia

The compounds of formula I and method of making and using the compounds of formula I are described in U.S. Pat. No. 4,826,868, issued May 2, 1989, incorporated by reference herein.

Tepoxalin is a potent inhibitor of both the cyclooxygenase and lipoxygenase pathways of the arachidonic acid cascade (U.S. Pat. No. 4,826,868 and Robinson, C., Drugs of the Future, 15, 9. 902 (1990)).

Known methods of synthesizing tepoxalin include the following. U.S. Pat. No. 4,826,868 describes reacting the alcohol, 5-(4-chlorophenyl)-1-(4-methoxyphenyl)-1H-pyrazole-3-propanol with Jones reagent to form the acid, 5-(4-chlorophenyl)-1-(4-methoxyphenyl)-1H-pyrazole-3-propanoic acid, which is reacted with dimethylformamide and oxalyl chloride in tetrahydrofuran ("THF") which is then reacted with methylhydroxylamine hydrochloride and triethylamine in THF.

U.S. Pat. No. 4,898,952 describes a process for making tepoxalin which comprises reacting a hydrazine with a diketoacid to form a pyrazole acid which is reacted with dimethylformamide and oxalyl chloride to yield the pyrazole acid chloride which is reacted with methyl hydroxylamine hydrochloride and triethylamine to yield tepoxalin. The diketoacid is prepared by adding an appropriately substituted acetophenone to a solution of lithium diisopropylamide (LDA made from diisopropylamine and n-butyllithium in THF at low temperature). Alternatively, lithium hexamethyl disilazide may be employed as the base in place of lithium diisopropylamide. Succinic anhydride is then added to this solution to produce the diketoacid.

U.S. Pat. No. 5,117,054 describes a process wherein p-chloroacetophenone is reacted with succinic anhydride to form 4-chloro-γ,ε-dioxo-benzenehexanoic acid which is reacted with acetic anhydride or acetyl chloride to yield 5-[2-(4-chlorophenyl)-2-oxoethylidene]dihydro-2(3H)-furanone. This compound is then added to a mixture of N-methylhydroxylamine hydrochloride and an amine base such as triethylamine, Hunig's base, pyridine or lutidine and a solvent such as methylene chloride or chloroform to form 4-chloro-N-hydroxy-N-methyl-γ,ε-dioxo-benzenehexanamide which is combined with 4-methoxyphenyl hydrazine hydrochloride, an amine base as described above in an alcoholic solvent such as methanol, ethanol or propanol.

The preparation of 4-chloro-γ,ε-dioxo-benzenehexanoic acid from p-chloroacetophenone utilizing various bases selected from lithium diisopropylamide (LDA); LDA.LiCl; magnesium diisopropylamide (MDA); MDA.1LiBr; MDA.2LiBR or lithium bis (trimethylsilyl) amide was disclosed in Murray et al, Synthesis 1991, p. 18–20.

Due to cost, toxicity, and hazard considerations, it is desirable to be able to synthesize 1,5-diaryl-3-substituted pyrazoles, particularly tepoxalin, without the reagents lithium hexamethyl disilazide, oxalyl chloride and methylene chloride and without excess p-chloroacetophenone.

The current invention produces tepoxalin in a much higher over-all yield and at a decreased cost than the known processes.

BRIEF SUMMARY OF THE INVENTION

The invention relates to a process for preparing a compound of the formula I

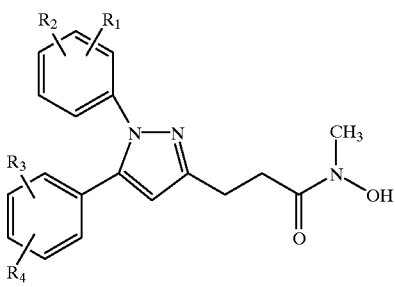

I

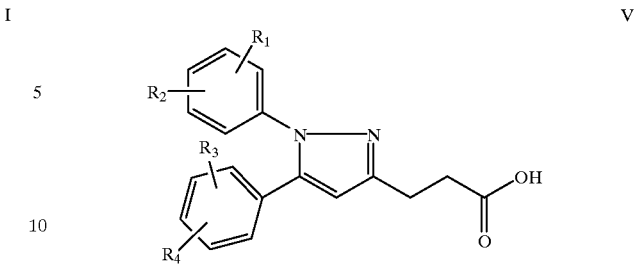

wherein $R_1$, $R_2$, $R_3$ and $R_4$ are as described above, reacting the compound of formula V with an alcohol to form the corresponding ester of formula VI

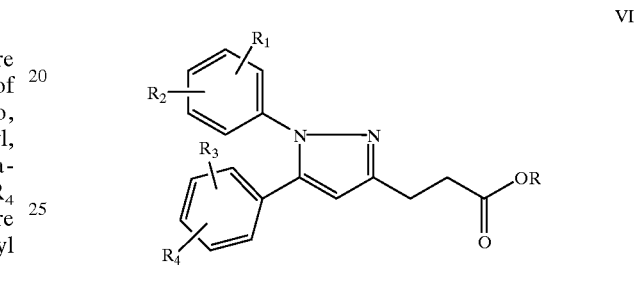

wherein $R_1$, $R_2$, $R_3$ and $R_4$ are as described above and R is lower alkyl or cycloalkyl, and reacting the ester of formula VI with N-methylhydroxylamine hydrochloride and a base to form the corresponding compound of formula I.

DETAILED DESCRIPTION OF THE INVENTION

In the above formula, $R_1$, $R_2$, $R_3$ and $R_4$ are substituents on phenyl rings, where phenyl rings substitute for hydrogen atoms at positions 1 and 5 of the pyrazole ring. It is preferred that at least one of $R_1$ and $R_2$, and one of $R_3$ and $R_4$ be substituted at the 4-positions of their respective phenyl rings.

Lower aklyl radicals include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, octyl and the like.

Lower alkoxy shall mean oxygen ethers formed from a before-described lower alkyl group. Exemplary radicals include methoxy, ethoxy, propoxy, isopropoxy, n-butoxy, and the like.

Lower alkylthio radicals of $R_1$, $R_2$, $R_3$ and $R_4$ are thio ethers and are thus analogous to the ethers described above.

Halo radicals preferably include chloro and bromo, as well as fluoro and iodo.

Lower alkylsulfonyl radicals contain a before-described lower alkyl radical bonded to an $SO_2$ moiety that is itself also bonded to a phenyl ring. Exemplary lower alkylsulfonyl radicals thus include methylsulfonyl, ethylsulfonyl, 2-ethylbutylsulfonyl and the like.

An omega-trifluoromethyl lower alkoxy radical is a lower alkoxy radical as before described that additionally includes a trifluoromethyl group at a position farthest on the alkyl chain from the place of bonding to the phenyl ring. Exemplary of such radicals are the 2,2,2-trifluoroethoxy.

Naphthyl and substituted naphthyl radicals can replace an aryl group herein at either the 1- or 2-positions to provide wherein $R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, omega-trifluoromethyl lower alkoxy, or where $R_1$, $R_2$ or $R_3$, $R_4$ taken together with the phenyl group to which they are attached, form a naphthyl or substituted naphthyl group;

comprising reacting a compound of formula II

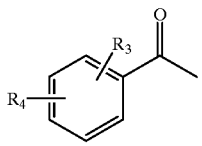

II wherein $R_3$ and $R_4$ are as described above, with succinic anhydride and an alkoxide base to form the corresponding compound of formula III

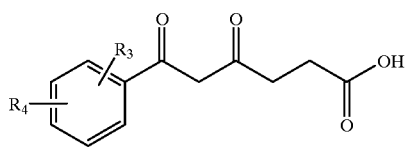

III wherein $R_3$ and $R_4$ are as described above, which is reacted with a compound of formula IV

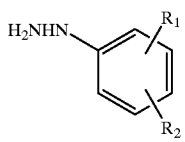

IV wherein $R_1$ and $R_2$ are as described above, to form a corresponding compound of formula V 1-naphthyl or 2-naphththyl substituents respectfully. Substituents on the naphthyl radicals can be any of those described herein as being useful aryl substituents. Exemplary substituted 1- and 2-naphthyls include 6-methoxy-2-naphthyl and the like.

As used herein, unless otherwise noted, the term "lower" when used with alkyl or alkoxy means a carbon chain composition of 1–6 carbon atoms.

The term "alkoxide base" refers to a lower primary alkoxide, secondary alkoxide, or tertiary alkoxide such as, methoxide, ethoxide, 2-propoxide, tert-butoxide and the like. The preferred base is a tertiary alkoxide and preferably potassium tert-butoxide.

The invention relates to a process of preparing a compound of the formula I

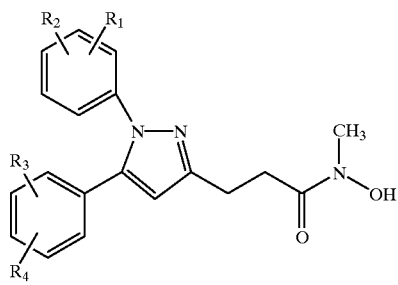

comprising reacting a compound of formula II

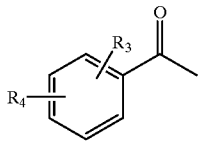

with succinic anhydride and an alkoxide base to form a corresponding compound of formula III

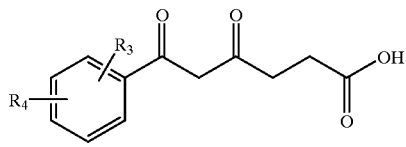

which is reacted with a compound of formula IV

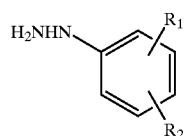

to form a corresponding compound of formula V

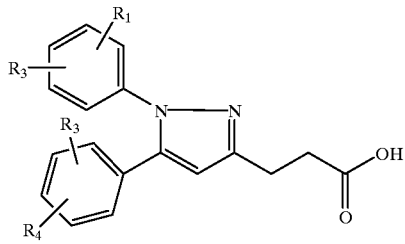

reacting the compound of formula V with an alcohol to form the corresponding ester of formula VI

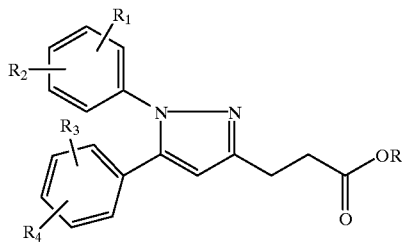

wherein R is lower alkyl, such as methyl, ethyl, isopropyl, preferably ethyl, or aryl, and reacting the ester of formula VI with N-methylhydroxylamine hydrochloride and an appropriate base, such as an alkoxide base, amine base or inorganic base such as NaOH or KOH, preferred is sodium ethoxide in ethanol, to form the corresponding compound of formula I.

In a preferred embodiment, the invention relates to a process of making compound of formula I wherein

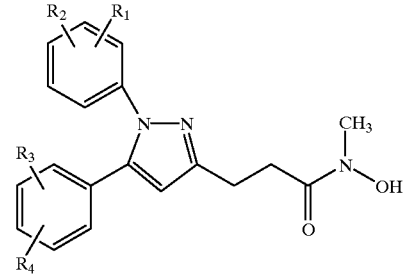

| $R_1$, $R_2$ | $R_3$, $R_4$ |
|---|---|
| 4-OEt | 4-Cl |
| 3,4-diOMe | 4-Cl |
| 2-OMe | 4-Cl |
| 4-OMe | 4-Me |
| 4-Cl | 4-OMe |
| 4-OMe | 4-OMe |
| 4-OMe | 4-H |
| 4-OMe | 3-Me |
| 4-OMe | 3,4-diMe |
| 4-OMe | 2,4,6-tri-Me |
| 4-OMe | 2-Me |
| 4-OMe | 4-Et |

-continued

| $R_1, R_2$ | $R_3, R_4$ |
|---|---|
| 4-OMe | 4-$CF_3$ |
| 4-OMe | 4-Cl |
| 4-OMe | 4-F |
| 4-H | 4-Cl |

In a particularly preferred embodiment, the invention relates to a process of making tepoxalin (Ia), wherein $R_1$ is 4-OMe and $R_3$ is 4-Cl, $R_2$ is H and $R_4$ is H.

SCHEME 1

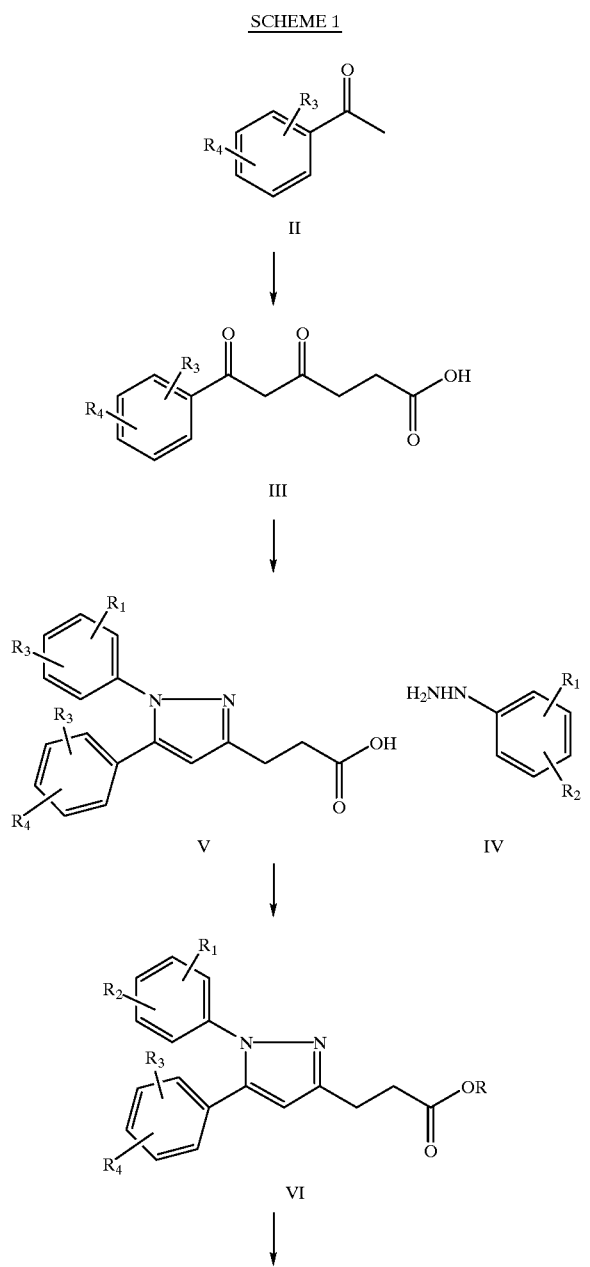

-continued

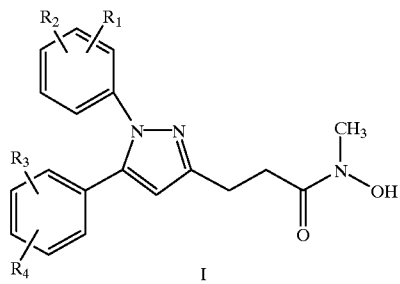

As set forth in Scheme 1, a compound of formula II, a known compound or compound prepared by known methods, is reacted with succinic anhydride and an alkoxide base such as Li, Na, or K tert-alkoxide, preferably K-tert-alkoxide, in a polar aprotic solvent such as dimethylformamide, (DMF) or THF, preferably DMF, preferably at an initial temperature from about −5 to 20° C., more preferably at 0–5° C., particularly preferred at 0° C., then heating to a temperature of 45–50° C. preferably at 45° C. to form the corresponding compound of formula III.

Preferably, 1 equivalent each of a compound of formula II, and succinic anhydride is reacted with 2 equivalents of an alkoxide base.

The compound of formula III is treated with, a compound of formula IV, a known compound or compound prepared by known methods, or preferably its HCl salt and a base such as $KHCO_3$, $NaHCO_3$, KOH, or NaOH, preferably $NaHCO_3$, in a lower alcohol solvent such as methanol, ethanol, or 2-propanol, preferably methanol, preferably at a temperature of from about 45 to 55° C., to form the corresponding compound of formula V. The compound of formula V is isolated by known methods preferably filtration to remove NaCl, seeding and cooling of the filtrate, and filtration to isolate the compound of formula V.

The compound of formula V is reacted in an alcohol solvent such as methanol, ethanol, 2-propanol, or benzyl alcohol, preferably ethanol, with a catalytic amount of an acid, such as sulfuric acid, hydrochloric acid, or p-toluene sulfonic acid at reflux temperature to produce the corresponding ester of formula VI (methyl, ethyl, isopropyl, or benzyl with ethyl being preferred).

The ester of formula VI is isolated by conventional means such as concentration, seeding, and filtration of the resulting solid. The ester of formula VI is treated with N-methylhydroxylamine hydrochloride (as a solid or as an alcoholic solution which has been prepared from an aqueous solution)and a base such as sodium methoxide, sodium ethoxide, sodium benzyl oxide or, sodium isopropoxide (preferably sodium ethoxide) or N-methyl hydroxylamine free base (a known compound) in an alcoholic. solvent such as methanol, ethanol, 2-propanol, or benzyl alcohol (preferably ethanol)to form the product of formula I. The product is isolated by known methods, preferably aqueous quench followed by filtration.

Alternatively, the ester of formula VI is not isolated. In this case, the compound of formula V is treated with an alcohol such as methanol, ethanol, isopropanol, or benzyl alcohol, preferably ethanol, and a catalytic amount of an acid such as sulfuric acid, hydrochloric acid, or p-toluene sulfonic acid and heated to reflux to form the ester of formula VI and the reaction cooled. The resulting solution of the ester of formula VI is reacted directly with N-methylhydroxylamine hydrochloride (as a solid or as an alcoholic solution which has been prepared from an aqueous solution) and basified with an appropriate base such as sodium methoxide, sodium ethoxide, sodium benzyl oxide or, sodium isopropoxide, preferably sodium ethoxide, to produce the product of formula I. The product is isolated by known methods, preferably aqueous quench followed by filtration.

Alternatively, neither the acid of formula V or the ester of formula VI is isolated, and the compound of formula III is converted (without isolation of V or VI) to product of formula I. In this case, the compound of formula III is treated with a compound of formula IV, a known compound or compound prepared by known methods, or preferably its HCl salt and a base such as $KHCO_3$, $NaHCO_3$, KOH, or NaOH, preferably NaOH, in a lower alcohol solvent such as MeOH, EtOH, or 2-propanol, preferably ethanol, preferably at a temperature of from about 20 to 55° C. (preferably at ambient temperature, approximately 25° C.) to form the corresponding compound of formula V. The resulting mixture of the compound of formula V is then treated with an acid, such as sulfuric acid, hydrochloric acid, or p-toluene sulfonic acid and heated to reflux to produce the corresponding ester of formula VI. The resulting reaction mixture of the ester of formula VI is then treated directly with N-methylhydroxylamine hydrochloride (as a solid or as an alcoholic solution which has been prepared from an aqueous solution) and basified with an appropriate base such as sodium methoxide, sodium ethoxide, sodium benzyl oxide or, sodium isopropoxide, preferably sodium ethoxide, to produce the corresponding product of formula I. The product is isolated by known methods, preferably aqueous quench followed by filtration.

In another embodiment, the claimed invention relates to a process of making an intermediate of formula III

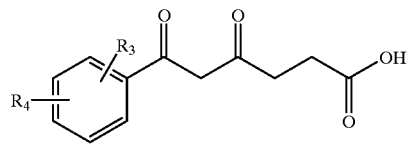

III comprising reacting a compound of formula II with succinic anhydride in an alkoxide base.

In addition, the claimed invention relates to a process for preparing 1,5-diaryl-3-substituted pyrazoles of formula I, particularly tepoxalin, comprising reacting a compound of formula V with an alcohol to form the corresponding ester of formula VI (where for example R=Me, Et, iPr, preferably Et) and reacting the corresponding ester of formula VI with N-methylhydroxylamine hydrochloride.

This invention also relates to the novel intermediate of formula VI (where for example R is methyl, ethyl or isopropyl preferably ethyl).

The following examples describe the invention in greater detail and are intended to illustrate the invention, but not to limit it.

EXAMPLE 1

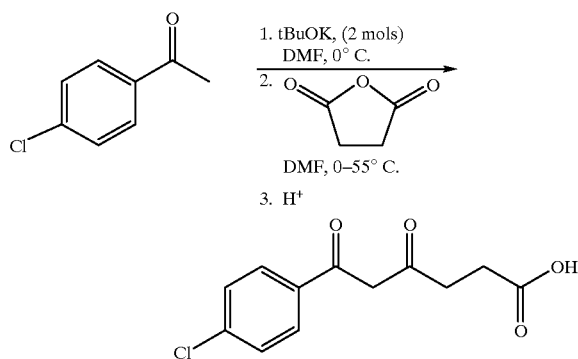

Potassium tert-butoxide (112.2 g 1 mol) was dissolved in DMF (250 mL) and cooled to 0° C. under a nitrogen atmosphere. p-chloroacetophenone (77.3 g, 0.5 mol) in DMF (50 mL) was added at 0° C. over about 30 min then stirred at 0° C. for 30 min. Succinic anhydride (50.0 g. 0.5 mol) was dissolved in DMF (170 mL) at room temperature (heating may be needed to dissolve succinic anhydride in DMF. The solution should be cooled to room temperature before it is added to the enolate solution) and was added to the above enolate solution at 0–5° C. over 80 min. The reaction mixture was stirred at 0–5° C. for 25 min, then heated to 55° C. for 30 min. The reaction mixture was quenched by adding water (400 mL) without external cooling; final temperature was about 52–55° C. Immediately following the quench, the reaction mixture was acidified to pH 5 with conc. HCl; final temperature was about 55–56° C. The reaction mixture became a light brown cloudy solution. The mixture was stirred and cooled to 5–10° C. The yellow solid product started forming at about 30° C. The resulting yellow solid was collected by filtration and washed with water (300 mL). After most of the water was drained, the solid was washed with toluene (250 mL) to remove any residual p-chloroacetophenone and most of the color. The solid was air-dried overnight. Yield: 68.8 g (53%).

EXAMPLE 2

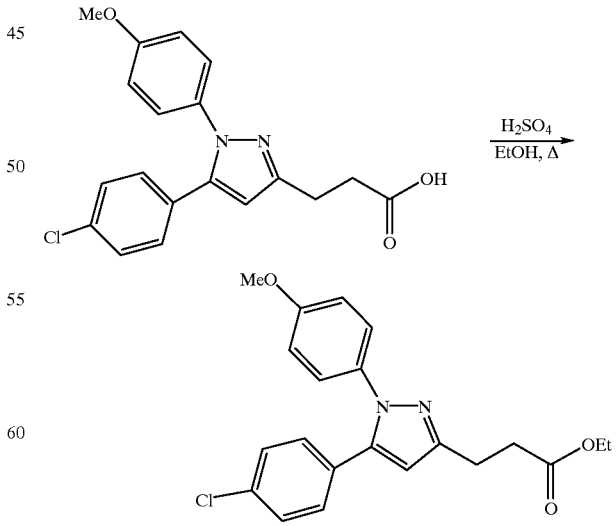

5-(4-chlorophenyl)-1-(4-methoxyphenyl)-1H-pyrazole-3-propanoic acid (300 g, 840 mmol) and ethanol (3 L) were placed in a flask. Concentrated H₂SO₄ (2.4 mL, 86.4 meq.) was added with stirring. The reaction was then heated to reflux. After approximately 30 minutes, the suspension dissolved. The reaction was monitored by TLC (silica gel; hexane:ethylacetate:methanol;70:20:10). After refluxing for 9 hours, all starting material was gone and 2 liters of ethanol was removed by distillation. The remaining solution was cooled with stirring to 0° C. and seeded with known ethyl-5-(4-chlorophenyl)-1-(4-methoxyphenyl)-1H-pyrazole-3-propanoate. The resulting suspension was stirred at 0° C. for 30 minutes and then filtered, washed with cold ethanol (100 mL) and vacuum dried (room temperature, ca. 5 mm Hg) to give ethyl-5-(4-chlorophenyl)-1-(4-methoxyphenyl)-1H-pyrazole-3-propanoate (275.0 g, 85% yield) as a clean white powder (mp=80–81° C.). An additional 27.9 g of ethyl-5-(4-chlorophenyl)-1-(4-methoxyphenyl)-1H-pyrazole-3-propanoate was obtained as a tan powder after reducing the volume of the mother liquor to approximately 100 mL and seeding with known ethyl-5-(4-chlorophenyl)-1-(4-methoxyphenyl)-1H-pyrazole-3-propanoate.

EXAMPLE 3

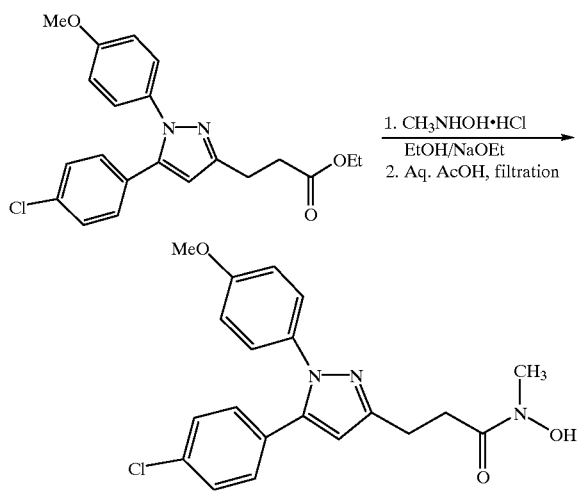

a) An oven-dried 1000 mL 3-necked round bottomed flask was equipped with an oven dried magnetic stirring bar, argon inlet, drying tube, thermometer, and an oven-dried 250 mL addition funnel. The flask was cooled to room temperature while supplying a stream of dry argon. The flask was charged with dry ethanol (160 mL) (200 proof undenatured ethanol dried with 4 A molecular sieves was used) via the addition funnel, and N-methylhydroxylamine hydrochloride (16.3 gm; 0.195 mole) was added to the stirring solvent to produce a clear colorless solution. The resulting mixture was cooled with an ice-water bath (1.0° C.) with stirring, and the addition funnel was charged with NaOEt (21 wt %, 170 mL; 0.46 mole). All of the NaOEt was added drop-wise to the cooled stirring solution of N-methylhydroxylamine hydrochloride over a 30 minute period (NaCl precipitated during the course of the addition, and the temperature rose to 6.0° C.). After stirring the resulting slurry approximately 15 minutes, the ethyl ester (ethyl-5-(4-chlorophenyl)- 1-(4-methoxyphenyl)-1H-pyrazole-3-propanoate) (50.0 gm; 0.13 mole) was added with good stirring. The resulting mixture was allowed to stir approximately 10 minutes, and then the reaction was allowed to warm to ambient temperature. The reaction was monitored by TLC (10% MeOH in CH₂Cl₂ for product, 50% EtOAc in hexane for starting material).

b) The reaction was allowed to stir for 16 hrs. The magnetic stirring bar was removed, and the flask was equipped with a mechanical stirrer and a 500 mL addition funnel. The reaction was cooled (2.5° C.) using an ice-water bath. The addition funnel was charged with a cooled (ice-water bath) mixture of glacial acetic acid (15 mL; 0.26 mole) and 330 mL of distilled water. The aqueous acetic acid mixture was added drop-wise to the reaction mixture with good stirring over a 30 minute period. The temperature rose to 7.8° C. during the course of the aqueous quench. After the addition of 155 mL of the aqueous acetic acid mixture, the reaction mixture turned into a clear brown solution. Product began to precipitate out slowly during the rest of the addition of the aqueous acetic acid mixture, and continued stirring and cooling after completion of the addition resulted in precipitation of more material. The pH at the end of the quench was between 6.4–6.8 as determined by litmus paper. The resulting milky brown mixture was stirred with continued cooling from the ice-water bath to allow full precipitation of the solid product. The ice-water bath was removed. The ethanol was removed from the reaction by distillation under vacuum (80 mm Hg) with heating up to 34.4° C. using a warm water bath. The mixture was cooled with an ice-water bath, and the pH was adjusted from 6.0 to between 6.4–6.8 with the addition of 21 mL of 1N NaOH. The resulting mixture was stirred 30 minutes with cooling from the ice-water bath, and the product was isolated by filtration through a course rated sintered glass funnel. The isolated solids were washed with ice-cold distilled water (2×75 mL). The product was air dried and then placed in a vacuum oven at 60° C. for 14.5 hours to provide crude tepoxalin as a light tan solid (48.38 gm; 96.5% yield).

c) A 1000 mL round bottomed 3-necked flask was equipped with a mechanical stirrer, condenser, and thermometer. The flask was charged with crude tepoxalin (48.18 gm; 0.125 mole) and 190 mL of ethyl acetate. The mixture was heated to reflux with good stirring to produce an amber solution. The solution was filtered hot through celite into another 1000 mL flask (product crystalized out upon cooling during filtration). The filtrate was heated to reflux to produce a clear amber solution. The solution was cooled to ambient temperature with stirring to bring about crystallization. After stirring 2 hrs at ambient temperature, the mixture was cooled using an ice-water bath and stirred for 3 hrs. The mixture was filtered, and the collected solids were washed with ice-cold ethyl acetate (2×50 mL). The product was air dried, and placed in a vacuum oven. The product was dried in the vacuum at 60° C. for 15 hrs to provide final product (45.08 gm; 89.9% yield, >99% HPLC wt % purity).

EXAMPLE 4

-continued

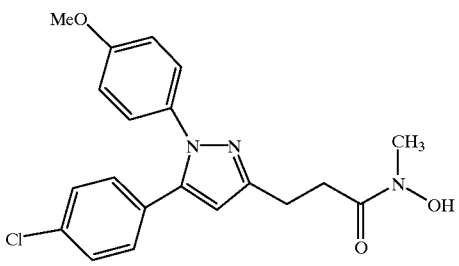

a) An oven dried 300 mL 3-necked round bottomed flask was equipped with a magnetic stirring bar, argon inlet, and drying tube. The flask was charged with 5-(4-chlorophenyl)-1-(4-methoxyphenyl)-1H-pyrazole-3-propanoic acid (10 gm, 28.03 mmol) followed by ethanol (100 mL). The resulting solution was cooled using an ice-water bath, the stirring solution was treated with concentrated $H_2SO_4$ (0.07 mL, 2.52 meq.). The flask was then removed from the ice-water bath, the argon inlet and drying tube were removed, and the flask was equipped with a condenser and thermocouple. The reaction mixture was heated to reflux and monitored by TLC (using a 1:2:6 MeOH:EtOAc:hexane solvent system). After stirring at reflux for 5 hours, the reaction flask was fitted with a short path distillation apparatus and ethanol was distilled off (70 mL). The resulting residue was cooled to 10° C. and treated dropwise with NaOEt (21 wt %, 37.7 mL, 101.04 mmol). The resulting mixture was then treated with N-methylhydroxylamine hydrochloride (3.51 gm; 42.05 mmol). The reaction flask was then re-equipped with a drying tube and argon inlet, and the reaction was stirred at ambient temperature.

b) The reaction was allowed to stir for 18 hours at ambient temperature. TLC analysis (using 50% EtOAc in hexane and 10% methanol in $CH_2Cl_2$) showed completion of the reaction. The reaction flask was placed in an ice-water bath, and the reaction mixture was treated dropwise with a cooled (ice-water bath) mixture of glacial acetic acid (3.3 mL; 57.4 mmol) and 33 mL of distilled water. After completion of the addition of the aqueous acetic acid solution, the pH of the mixture was adjusted to between 6.4 to 6.8 with 1N NaOH (litmus). The mixture was then treated with additional distilled water (5 mL) where upon solid began to precipitate out. The reaction flask was then equipped with a short path distillation apparatus, and approximately 27 mL of solvent was removed (80 mm of Hg vacuum at 30–35° C.). The pH of the resulting mixture was re-adjusted to between 6.4 to 6.8, and the mixture was allowed to stir with cooling from an ice-water bath for 30 minutes. The solid was collected by filtration, and the solid product was washed with ice-cold distilled water. The air-dried product was then placed in a vacuum oven and dried for 18 hours at 60° C. under vacuum to give 9.51 gm of tepoxalin (87.9% yield, HPLC wt % purity of 98.6%).

EXAMPLE 5

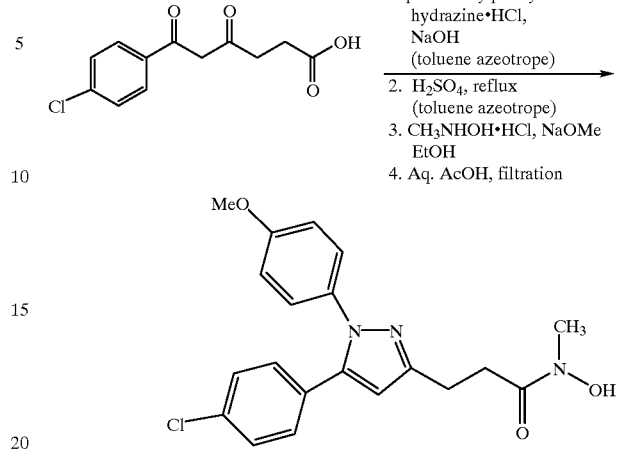

a) An oven-dried 250 mL 3-necked round bottomed flask was equipped with an argon inlet, drying tube, and magnetic stirring bar. A stream of dry argon was supplied, and the flask was charged with 4-chloro-γ,ε-dioxo-benzenehexanoic acid (10 gm; 39.27 mmol), p-methoxy phenyl hydrazine hydrochloride (11.32 gm; 42.78 mmol and anhydrous ethanol (80 mL, denatured with toluene). The resulting slurry was cooled with stirring using an ice-water bath. The mixture was treated with powdered NaOH (1.73 gm; 43.25 mmol). The mixture was stirred at room temperature for 14 hours to bring about completion of the reaction (monitor the reaction by thin layer chromatography using 5% MeOH in methylene chloride developing the plate 4–5 times with U.V. detection). The reaction flask was fitted with a short path distillation apparatus, and solvent was removed under reduced pressure. (A vacuum of approximately 40 mm of Hg was used for the vacuum distillation.) The residue from the vacuum distillation was azeotropically dried with toluene (2×40 mL). (A vacuum of approximately 40 mm of Hg was used for the azeotroping.) Ethanol (66 mL) was added to the residue, and the mixture was stirred to produce a fine suspension. The suspension was treated with concentrated sulfuric acid (0.1 mL; 3.6 meq), and the mixture was heated to reflux. The reaction was stirred at reflux for 16 hours (the reaction mixture becomes very dark upon the addition of the sulfuric acid). Monitor the reaction by TLC (10% MeOH in methylene chloride). The solvent was then removed under reduced pressure via a short path distillation apparatus to produce an oily residue. (A vacuum of approximately 40 mm of Hg was used for the vacuum distillation.)

The residue from the vacuum distillation was azeotropically dried with toluene using a short-path distillation apparatus (2×40 mL). (A vacuum of approximately 40 mm of Hg was used for the azeotroping. The product crystallized out during the azeotroping process.) The resulting residue was diluted in ethanol (66 mL), and the mixture was stirred at reflux for 1 hr. The mixture was cooled to room temperature and then to 50° C. using an ice-water bath- The reaction was treated with N-methyl hydroxylamine HCl (4.92 gm; 58.91 mmol) followed immediately with NaOMe (33 mL of a 25 wt % solution; 144.21 mmol) with drop-wise addition via an oven-dried dropping funnel over 20 minutes with good stirring.

b) The resulting reaction mixture was stirred at room temperature for 16 hrs (monitor the reaction with TLC 50% EtOAc in hexane). Solvent was removed from the reaction via a short path distillation apparatus under reduced pressure. (A vacuum of approximately 40 mm of Hg was used for the vacuum distillation). Ethanol (20 mL) was added to the thick reaction mixture to allow stirring. The reaction was cooled to 5° C. using an ice-water bath and a solution of aqueous acetic acid (4.6 mL of glacial acetic acid; 80.04 mmol, in 66 mL of water) was slowly added. The reaction mixture turned clear, and the mixture was seeded with pure tepoxalin. Quenching the reaction with slow addition of the aqueous acetic acid solution with seeding (total addition time approximately 20 minutes) was continued. By the end of the addition, solid product precipitated out. The pH of the reaction was adjusted to between 6.8–7.0, and the resulting mixture was warmed to room temperature with stirring. (The pH of the reaction was adjusted from pH 9 to between 6.8–7.0 using glacial acetic acid.)

The resulting slurry was stirred at room temperature for 1 hr. and ethanol was removed from the reaction at reduced pressure via a short path distillation apparatus. (A vacuum of approximately 40 mm of Hg was used for the vacuum distillation with a maximum temperature of 28° C. being obtained.) The pH of the reaction was adjusted to between 6.8–7.0, and the resulting mixture was stirred for 2 hrs in an ice-water bath. The mixture was filtered through a coarse rated sintered glass funnel and the solid was washed with distilled water (5×60 mL). The collected solid was air dried, and then the solid was dried under vacuum at 65° C. for 12 hrs to obtain crude tepoxalin (13.09 gm; 86.39% crude yield; HPLC wt % purity of 95.26%) as a brown solid.

c) A 250 mL round-bottomed three necked flask equipped with magnetic stirring bar and condenser was charged with crude tepoxalin (12.90 gm). The crude product was treated with EtOAc (50 mL), and the resulting slurry was heated to reflux to produce a clear dark-brown solution. The hot solution was filtered through celite, and the celite was washed with hot EtOAc (5 mL). (Product crystallized out during filtration.) The filtrate was heated to reflux to dissolve product that had crystallized out, and the mixture was cooled slowly to room temperature. The mixture was stirred at room temperature for 1.0 hr and then with cooling from an ice-water bath for 2 hrs. The resulting solid was collected by filtration and the product was washed with ice-cold EtOAc (3×13 mL). After air-drying, the product was oven dried at 70° C. for 42 hrs to produce purified tepoxalin (11.25 gm) as a slightly brown solid (87.21% recovery, >99.9% HPLC wt % purity).

EXAMPLE 6

Preparation of an Alcoholic Solution of N-Methylhydroxylamine HCl

A 500 mL one necked round-bottomed flask was charged with an aqueous solution of N-methylhydroxylamine HCl (30 mL) and toluene (250 mL). The flask was fitted with a Dean-Stark trap, and approximately 15 mL of water was distilled off. The Dean-Stark trap was replaced with a short path distillation apparatus, and the remaining toluene was distilled off. The resulting residue was then dissolved into anhydrous ethanol (250 mL). $^1$H NMR analysis gave a molarity of approximately 0.83 M.

What is claimed:

1. A process for preparing a compound of the formula I

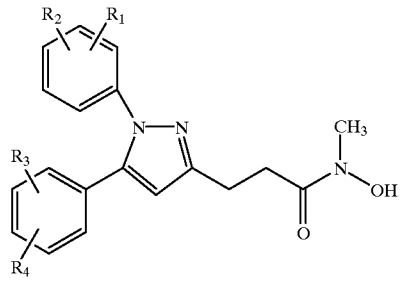

wherein $R_1$, $R_2$, $R_3$ and $R_4$ are the same or different and are individually selected from the group consisting of hydrogen, lower alkyl, lower alkoxy, amino, acetamido, phenyl, halo, hydroxy, lower alkylsulfonyl, lower alkylthio, nitro, trifluoromethyl, omega-trifluoromethyl lower alkoxy, or where $R_1$, $R_2$ or $R_3$, $R_4$ taken together with the phenyl group to which they are attached, form a naphthyl or substituted naphthyl group;

comprising reacting a compound of formula II

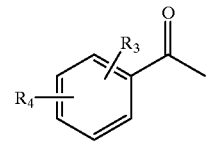

wherein $R_3$ and $R_4$ are as described above, with succinic anhydride and an alkoxide base to form a compound of formula III

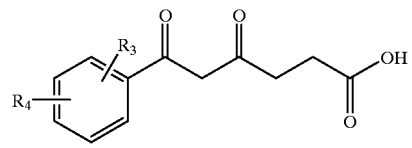

wherein $R_3$ and $R_4$ are described above, reacting the compound of formula III with a compound of formula IV

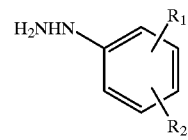

wherein $R_1$ and $R_2$ are as described above, to form a compound of formula V which is isolated

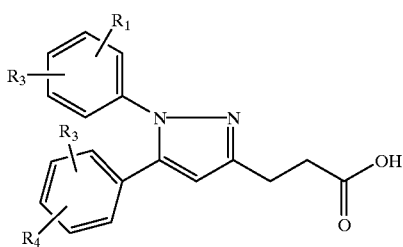

V reacting the compound of formula V with an alcohol to form the corresponding ester of formula VI

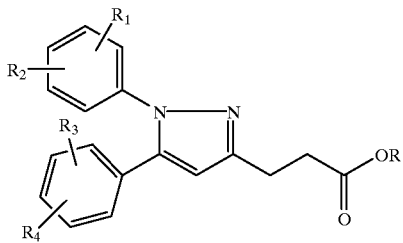

VI wherein R is lower alkyl, which is isolated and reacting the isolated ester with N-methylhydroxylamine hydrochloride to form the compound of formula I.

2. A process of claim 1, wherein $R_1$ and $R_2$ are independently selected from the group consisting of hydrogen, 4 ethoxy, 3,4-dimethoxy, 2-methoxy, 4-methoxy, and 4-chloro.

3. A process of claim 2, wherein $R_3$ and $R_4$ are independently selected from hydrogen, 4-chloro, 4-methyl, 3,4-dimethyl, 2,4,6-trimethyl, 2-methyl, 4-ethyl, $4CF_3$, 4-fluoro and 4-methoxy.

4. A process of claim 3, wherein $R_1$ is 4-methoxy, and $R_3$ is 4-Cl, $R_4$ is H and $R_2$ is H.

* * * * *